United States Patent [19]

Hölscher

[11] Patent Number: 4,624,261
[45] Date of Patent: Nov. 25, 1986

[54] ELECTROCHEMICAL MEASURING CELL HAVING AN ANCILLARY ELECTRODE

[75] Inventor: Uvo Hölscher, Stockelsdorf, Fed. Rep. of Germany

[73] Assignee: Drägerwerk Aktiengesellschaft, Lübeck, Fed. Rep. of Germany

[21] Appl. No.: 771,995

[22] Filed: Sep. 3, 1985

[30] Foreign Application Priority Data

Sep. 7, 1984 [DE] Fed. Rep. of Germany ....... 3432950

[51] Int. Cl.[4] .................. A61B 5/04; G01N 27/52
[52] U.S. Cl. .................................. 128/635; 128/639; 128/644; 128/670; 204/403; 204/412; 204/415
[58] Field of Search .............. 128/635, 639, 644, 670; 204/403, 412, 415, 1 P

[56] References Cited

U.S. PATENT DOCUMENTS

| | | | |
|---|---|---|---|
| 3,468,781 | 9/1969 | Lucero | 204/415 |
| 3,708,412 | 1/1973 | Lofgren | 204/415 |
| 4,517,982 | 5/1985 | Shiga et al. | 128/635 |
| 4,538,617 | 9/1985 | Jensen | 128/635 |

FOREIGN PATENT DOCUMENTS

| | | | |
|---|---|---|---|
| 2930663 | 2/1981 | Fed. Rep. of Germany | 128/635 |
| 54344 | 5/1981 | Japan | 204/415 |
| 56-748 | 4/1982 | Japan | 204/415 |

*Primary Examiner*—G. L. Kaplan
*Attorney, Agent, or Firm*—Walter Ottesen

[57] ABSTRACT

An electrochemical measuring cell is disclosed having a device for sensing an external electrical potential. The device is arranged in the region of the outer surface of the diffusion membrane of the cell. The device can be, for example, in the form of a conductive, gas permeable coating applied to the outer surface of the diffusion membrane.

5 Claims, 1 Drawing Figure

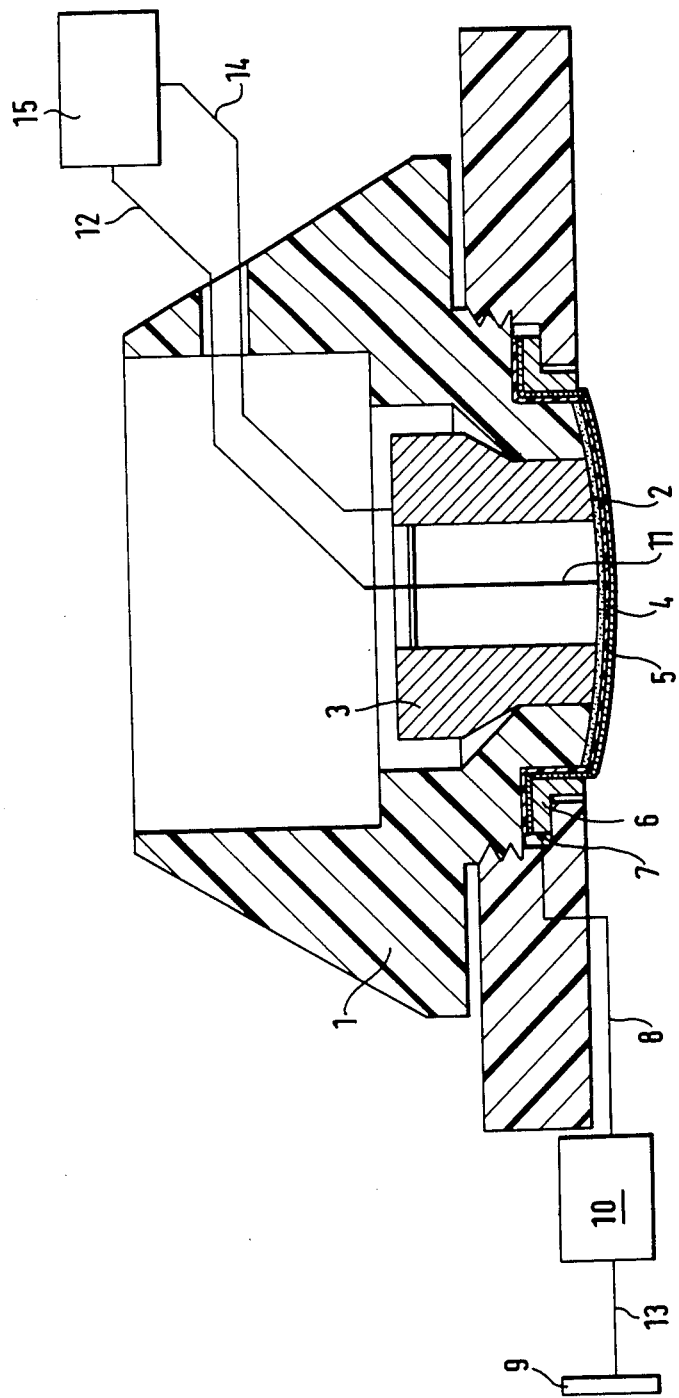

`4,624,261`

ELECTROCHEMICAL MEASURING CELL HAVING AN ANCILLARY ELECTRODE

FIELD OF THE INVENTION

The invention relates to an electrochemical measuring cell which includes a counter electrode and a measuring electrode disposed in an electrolyte. The electrolyte is separated from the ambient by means of a diffusion membrane. The electrochemical measuring cell further includes an arrangement for additionally sensing an external electrical potential.

BACKGROUND OF THE INVENTION

An electrochemical measuring cell of the above type is disclosed in European Patent Application No. A2 0077054. This measuring cell includes a first electrode arrangement which is sealed off with respect to the ambient by means of a diffusion membrane. The first electrode arrangement is surrounded by a second annular electrode with the corresponding counter electrode mounted on the rearward end of the head of the measuring cell. The ancillary electrode arrangement can, for example, be utilized to record bio-electrical quantities (Electrocardiogram).

In the known transducer, the ancillary annular electrode is held in a threaded ring disposed in surrounding relationship to the measuring head. Consequently, the measuring cell has such a size that it is unsuitable for placement in smaller openings. Furthermore, with the overall size otherwise being the same, the adhering surface for attaching the measuring cell to a support such as the skin of a person or the hide of an animal is reduced in such a manner that a reliable adherence is no longer assured for difficult conditions which often occur in practice.

SUMMARY OF THE INVENTION

It is an object of the invention to improve the known transducers so that a device for additionally sensing an external electrical potential can be mounted on the measuring cell without taking up space for itself thereby increasing the available adhering surface.

The above object is realized in that the device is mounted in the outer surface region of the diffusion membrane.

With the arrangement of the device pursuant to the invention, a large surface electrode for sensing an external electrical potential is provided. By placing the device in the region of the diffusion membrane, a utilization of surface is achieved which is subtle in its application.

In an advantageous embodiment of the invention, the device can be a coating which is applied to the outer surface of the membrane and can, for example, be a metal or graphite layer with a wire mesh or grid made of conductive material embedded therein.

In a further advantageous embodiment of the invention, the diffusion membrane itself can be made of a conductive plastic. Such a conductive plastic is preferably polypyrrole. However, there are also other known conductive plastics which can be used. In addition, if such conductive plastics are electrochemically active substances or are themselves electrochemically active, such a diffusion membrane can at the same time serve as the measuring electrode of the electrochemical cell.

BRIEF DESCRIPTION OF THE DRAWING

The drawing consists of one FIGURE showing an elevation view, partially in section, of an embodiment of the electrochemical measuring cell of the invention.

DESCRIPTION OF THE PREFERRED EMBODIMENTS OF THE INVENTION

The electrochemical measuring cell includes a housing 1 which contains the electrolyte 2 and the counter electrode 3. The housing 1 is sealed off with respect to the ambient by a diffusion membrane 4. An electrically conductive coating 5 is applied to the outer surface of the diffusion membrane 4. The coating 5 extends so far that the clamping ring 6 is in electrical contact with the coated diffusion membrane 4 so that the external electrical potential can be taken off on the clamping ring 6, and conducted via the contact 7 and the lead 8 to an evaluation unit 10. A second measuring input of the evaluation unit 10 is connected via a connecting lead 13 to a reference electrode 9. The measuring electrode 11 is connected with the measuring device 15 via lead 12 and the counter electrode 3 is connected with the measuring device 15 via lead 14 so that the measuring device 15 can evaluate the measuring signals of the electrochemical cell.

It is understood that the foregoing description is that of the preferred embodiments of the invention and that various changes and modifications may be made thereto without departing from the spirit and scope of the invention as defined in the appended claims.

What is claimed is:

1. An electrochemical measuring cell comprising:
an electrolyte;
a measuring electrode disposed in said electrolyte;
a counter electrode also disposed in said electrolyte;
a housing for holding said electrolyte;
a diffusion and sensing member including a diffusion membrane for separating said electrolyte from the ambient and having an outer surface facing away from said electrolyte; and, a coating applied to said outer surface of said diffusion membrane for sensing an external electrical potential, said coating being electrically conductive and permeable to gas; and,
electric circuit means mounted on said housing for conducting said external potential away from said coating and making the same accessible for measurement.

2. An electrochemical measuring cell comprising:
an electrolyte;
a measuring electrode disposed in said electrolyte;
a counter electrode also disposed in said electrolyte;
holding means for holding said electrolyte;
a diffusion membrane for separating said electrolyte from the ambient and having an outer surface facing away from said electrolyte, said diffusion membrane being made of an electrically conductive plastic so as to permit the same to sense an external electrical potential.

3. The electrochemical measuring cell of claim 2, said diffusion membrane being made of polypyrrole.

4. An electrochemical measuring cell comprising:
an electrolyte;
a measuring electrode disposed in said electrolyte;
a counter electrode also disposed in said electrolyte;
a housing for holding said electrolyte; and, a diffusion and sensing member including a diffusion membrane for separating said electrolyte from the ambient and having an outer surface facing away from said electrolyte; and, a gas permeable layer applied to said outer surface of said diffusion membrane for sensing an external potential, said layer being a metal layer having a wire mesh made of conductive material embedded therein.

5. An electrochemical measuring cell comprising:
an electrolyte;
a measuring electrode disposed in said electrolyte;
a counter electrode also disposed in said electrolyte;
a housing for holding said electrolyte; and,
a diffusion and sensing member including a diffusion membrane for separating said electrolyte from the ambient and having an outer surface facing away from said electrolyte; and, a gas permeable layer applied to said outer surface of said diffusion membrane for sensing an external potential, said layer being a graphite layer with a wire mesh embedded therein.

* * * * *